United States Patent [19]

Koch

[11] Patent Number: 5,747,465
[45] Date of Patent: May 5, 1998

[54] SUGAR DERIVATIVES OF MACROLIDES

[75] Inventor: Kevin Koch, Mystic, Conn.

[73] Assignee: Pfizer Inc., New York, N.Y.

[21] Appl. No.: 284,504

[22] PCT Filed: Jan. 28, 1993

[86] PCT No.: PCT/US93/00470

§ 371 Date: Aug. 8, 1994

§ 102(e) Date: Aug. 8, 1994

[87] PCT Pub. No.: WO93/18050

PCT Pub. Date: Sep. 16, 1993

[51] Int. Cl.$^6$ .............. A61K 31/70; C07H 17/08
[52] U.S. Cl. .............. 514/28; 536/6.5; 536/7.1; 536/18.1
[58] Field of Search .............. 536/6.5, 7.1, 18.6, 536/18.1; 514/28

[56] References Cited

U.S. PATENT DOCUMENTS

| 4,046,878 | 9/1977 | Patelli et al. .............. 536/64 |
| 4,894,366 | 1/1990 | Okuhara et al. .............. 514/63 |

FOREIGN PATENT DOCUMENTS

| 0323042 | 7/1989 | European Pat. Off. . |
| 0428365 | 5/1991 | European Pat. Off. . |
| 0466365 | 1/1992 | European Pat. Off. . |
| WO9102736 | 3/1991 | WIPO . |

*Primary Examiner*—Elli Peselev
*Attorney, Agent, or Firm*—Peter C. Richardson; Gregg C. Benson

[57] ABSTRACT

This invention relates to the saccharide derivatives of macrocyclic compounds useful for the treatment of resistance to transplantion, autoimmune disease and fungal diseases.

22 Claims, No Drawings

SUGAR DERIVATIVES OF MACROLIDES

BACKGROUND OF THE INVENTION

This invention relates to new chemical compounds which have value in the field of medical science. More particularly, it relates to new chemical compounds which are of value for administration to a mammalian subject, particularly man, as immunosuppressive agents. These new immunosuppressive agents can be compared to the macrolides known as FK-506 and FK-520, which are described in further detail in U.S. Pat. No. 4,894,366. The new compounds of this invention will find special utility in preventing or treating graft rejection following skin or organ transplant surgery and in preventing or treating autoimmune diseases such as rheumatoid arthritis and psoriasis. Additionally, these macrolide derivatives will find use in preventing or treating infectious diseases caused by fungi.

Graft or organ transplant rejection following transplant surgery is a common occurrence which arises when foreign antigens are recognized by the host's immune response system. The host's immune response system, in an effort to "protect" itself from the foreign tissue, then releases its cellular and humoral arsenal. The antibodies attack the foreign tissue, resulting in complications which often end in rejection of said tissue.

Similarly, the occurrence of immunoregulatory irregularities in autoimmune and chronic inflammatory diseases is well known. Irrespective of the underlying etiology of the condition, a variety of autoantibodies and self-reactive lymphocytes often arise to complicate the condition.

Treatments which target the immune response system often result in a complete shutdown of the system, leading to a lowering of the body's ability to combat infection. This can be as dangerous as the original condition which led to the shutdown.

Currently the leading medicinal agent for the prevention or treatment of graft rejection is cyclosporin A, approved by the United States Food and Drug Administration in 1983. The drug acts by inhibiting the body's immune response system from mobilizing its arsenal of natural protecting agents to reject the transplant's foreign protein. Although cyclosporin is effective in fighting graft rejection, it suffers drawbacks in that it can cause kidney failure, liver damage and ulcers; which in many cases can be very severe. Safer drugs which are more selective in their ability to affect the immune response system and which have fewer side effects are constantly being pursued.

U.S. Pat. No. 4,894,366 discloses the macrolides FK-506 and FK-520, inter alia, as immunosuppressants, including the treatment of "resistance to transplantation," autoimmune diseases and infectious diseases. International Patent Publication No. WO 91/02736 discloses derivatives of FK-506, FK-520 and related macrolides. European Patent Publication No. 428,365 A1 discloses various other derivatives of FK-506, FK-520 and related macrolides.

SUMMARY OF THE INVENTION

The present invention is directed to compounds of the formula

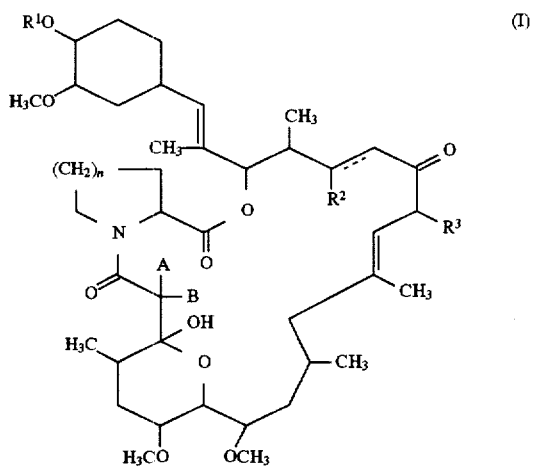

or a pharmaceutically acceptable salt thereof;

wherein n is 1 or 2;

the dotted line represents an optional double bond in the case where $R^2$ is H;

A and B are taken separately and A is H and B is H or OH, or A and B are taken together and form =O;

$R^2$ is H, ($C_2$–$C_5$)alkanoyloxy or —$OR^o$;

$R^3$ is ($C_1$ to $C_3$)alkyl or allyl;

$R^1$ and $R^o$ are each H,

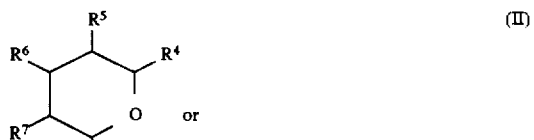

$R^4$ is, for each occurrence, independently —$CO_2R^8$, —$CO_2H$, —$CH_2OH$, H, —$CH_3$, —$CONH_2$, —$CONHR^8$, —$CONR_2^8$, —$CH_2OCOR^8$, —$CH_2OCO_2R^8$, —$CH_2OCONHR^8$, —$CH_2OCONR_2^8$ or —$CH_2OR^8$;

$R^5$, $R^6$ and $R^7$ are, for each occurrence, independently ($C_1$ to $C_4$)alkoxy, benzyloxy, —OH, —$OCOR^8$, —$OCO_2R^8$ or —$OSi(R^9)_3$;

$R^8$ is ($C_1$–$C_6$)alkyl, ($C_3$–$C_6$)cycloalkyl, allyl, pyridyl, thienyl, benzyl, benzyl variously substituted with one to five halogen atoms, —OH groups or ($C_1$–$C_4$)alkoxy groups, phenyl or phenyl variously substituted with one to five halogen atoms, —OH groups or ($C_1$ to $C_4$)alkoxy groups; and $R^9$ is, for each occurrence, independently ($C_1$ to $C_4$)alkyl, phenyl or benzyl; provided that $R^1$ and $R^o$ are not both H; and provided that when $R^o$ is

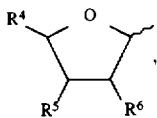 (III)

R¹ is not H.

A preferred group of compounds of this invention is the group of compounds of formula (I) wherein the dotted line represents no bond and R² is —OH.

A more preferred group of compounds of this invention within the preferred group of compounds are those compounds wherein n is 2; the dotted line represents no bond; A and B are taken together and form =O; R² is —OH; R³ is ethyl; R¹ is

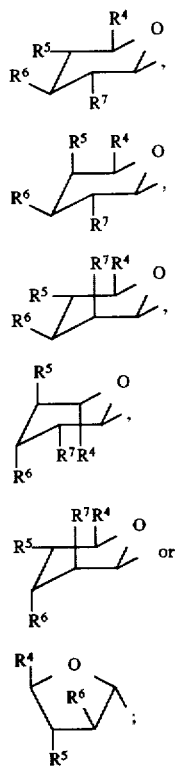

R⁴ is —CH₂OH, —CH₃, —CH₂OCOCH₃, —CH₂OCOCH₂C₆H₅ or —CO₂CH₃; and R⁵, R⁶ and R⁷ are each, independently, —OH, —OCOCH₃ or —OCOCH₂C₆H₅.

Especially preferred within this group are the compounds where R¹ is

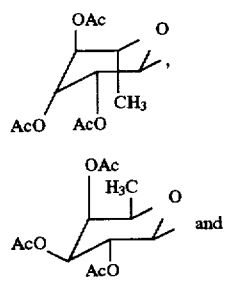

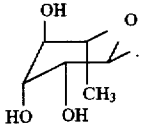

A second preferred group of compounds of this invention is the group of compounds of formula I wherein n is 2; A and B are taken separately and are each H; the dotted line represents no bond; R² is —OH; and R³ is ethyl.

The compounds of formula (I) are active as immunosuppressants. This activity makes these compounds useful in treating and preventing graft and transplant rejection. Further, this activity makes these compounds useful in preventing and treating autoimmune diseases such as rheumatoid arthritis and psoriasis in a mammal, especially man.

Accordingly this invention also embraces a method of treating resistance to transplantation in a mammal in need of such treatment comprising administering to said mammal a compound of formula (I) or a pharmaceutically acceptable salt thereof.

The term "transplantation," when used above and hereinafter, refers to the implantation in one part of an individual of a tissue or organ taken from another part of that individual or from another individual. Typical transplantations include, but are not limited to, bone marrow, heart, renal, tendon and pancreaticoduodenal transplantations.

The term "graft" when used above and hereinafter, refers to any unattached tissue or organ which is used for transplantations. Typical grafts include, but are not limited to, skin, bone, fat and nerve grafts.

Additionally this invention embraces a method of treating autoimmune disease (such as rheumatoid arthritis or psoriasis) in a mammal in need of such treatment comprising administering to said mammal a compound of formula (I) or a pharmaceutically acceptable salt thereof.

Further, this invention embraces a pharmaceutical composition comprising a resistance to transplantation treating effective amount of a compound of formula (I) and a pharmaceutically acceptable carrier.

Still further this invention embraces a pharmaceutical composition comprising an autoimmune disease (such as rheumatoid arthritis or psoriasis) treating effective amount of a compound of formula (I) and a pharmaceutically acceptable carrier.

Yet further the compounds of this invention of formula (I) have antifungal activity. Hence these compounds can be used to treat or prevent infections in mammals caused by fungi.

Accordingly, this invention embraces a method of treating diseases caused by fungi in a mammal in need of such treatment comprising administering to said mammal an effective amount of a compound of formula (I) or a pharmaceutically acceptable salt thereof.

Additionally, this invention embraces a pharmaceutical composition comprising a fungal infectious disease treating effective amount of a compound of formula (I) and a pharmaceutically acceptable carrier.

DETAILED DESCRIPTION

The compounds of formula (I) of the present invention are readily prepared. Most generally, a macrolide of formula (IV) or (V) below

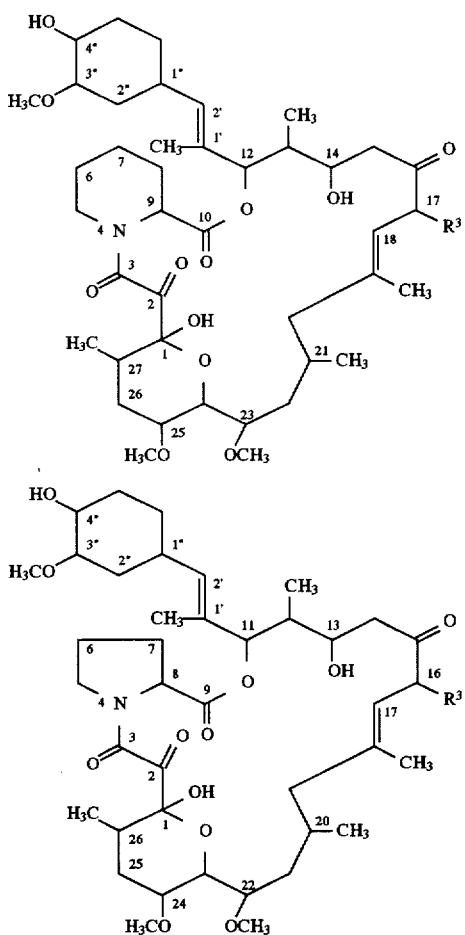

is coupled with an appropriate sugar halide derivative of the formula

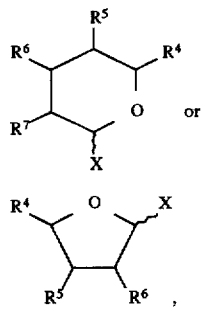

wherein X is halo, such as bromo or chloro. The coupled (or glycosylated) macrolide is then further modified as described hereinbelow.

The production of macrolides of formulae (IV) and (V) is well-known in the literature. The generally preferred route to these macrolides is via biological fermentation of microorganisms belonging to the genus Streptomyces. The compounds of formulae (IV) and (V) wherein $R^3$ is allyl are obtained by fermentation of Streptomyces tsukubaensis No. 9993 (Ferm BP-927). The compound of formula (IV) wherein $R^3$ is ethyl and the compound of formula (IV) wherein $R^3$ is methyl are obtained by fermentation of Streptomyces hygroscopicus subsp. ascomyceticus ATCC 14891.

A lyophilized sample of Streptomyces hygroscopicus subsp. ascomyceticus ATCC 14891 has been deposited with the American Type Culture Collection, 12301 Parklawn Drive, Rockville, Md., 20852, U.S.A., under the terms of the Budapest Treaty on Jan. 13, 1992. This newly deposited culture was given the new deposit number of ATCC 55276.

Streptomyces tsukubaensis No. 9993 (Ferm BP-927) is currently on deposit with the Fermentation Research Institute, Agency of Industrial Science and Technology (No. 1–3, Higashi-1-chome, Yatabemachi, Tsukuba-gun, Ibaraki Prefecture, Japan), under the provisions of the Budapest Treaty. A fresh sample of the microorganism will be deposited with the American Type Culture Collection in accordance with the terms of the Budapest Treaty.

The above-mentioned microorganisms, when placed separately in aqueous nutrient media, will produce the aforementioned compounds of formulae IV and V. The fermentation of said microorganisms to produce these macrolides is accomplished substantially as disclosed in U.S. Pat. No. 4,894,366, which is hereby incorporated by reference. Any changes made to the disclosed procedure are made in order to accommodate existing equipment at the facility and are described in Preparations 1 and 2 hereinbelow.

To prepare the compound of formula (I) wherein $R^0$ is H and $R^1$ is a sugar substituent of formula (II) or (III), a macrolide of formula (IV) or (V) is coupled with a sugar halide of formula (VI) or (VII).

The coupling (or glycosylation) reaction of a sugar halide of formula (VI) or (VII) and a macrolide of formula (IV) or (V) is accomplished in a straightforward manner, using chemistry well known to one of ordinary skill in the art. The coupling reaction is generally carried out using the peracetylated form of the sugar. About 2–4 molar equivalents of the appropriate sugar halide of formula (VI) or (VII) is mixed with the macrolide of formula (IV) or (V) in a reaction inert solvent. Reaction inert solvents useful for this type of reaction include chlorinated solvents such as chloroform, methylene chloride and ethylene dichloride; ether solvents such as diethyl ether, tetrahydrofuran, dioxane and dimethoxyethane; aromatic solvents such as benzene, toluene and xylene; and dipolar aprotic solvents such as N,N-dimethylformamide, acetonitrile and N-methyl-pyrrolidone. Preferred solvents are chlorinated solvents and a particularly preferred solvent is methylene chloride. Generally it is desirable to employ enough solvent such that the reactants are dissolved or suspended by the solvent. Typically the amount of solvent used is varied to give a $10^{-1}$ to $10^{-3}$ Molar solution of macrolide with $10^{-1}$ Molar being preferred. Dry conditions are maintained during the course of the reaction by the utilization of anhydrous solvents and by the addition of a drying agent to the reaction mixture. Drying agents typically used for this purpose are molecular sieves, calcium sulfate and magnesium sulfate. A preferred drying agent is 4 Å molecular sieves. Initial mixing of the reagents is performed at a temperature of from about −78° C. to about 70° C. Preferred are temperatures ranging from about −78° C. to about 0° C. Especially preferred for ease of preparation is a cooling bath which maintains the reaction temperature at −78° C.

After the above-mentioned reactants have been mixed and the temperature has equilibrated to −78° C., the reaction mixture is treated with a suitable base such as mercuric carbonate, silver carbonate, mercuric nitrate or silver nitrate. The preferred base for this reaction is silver carbonate. Following addition of said base, the reaction mixture is treated with a catalyst. Typical catalysts for this reaction include triflate, perchlorate and tetrafluoroborate salts of the cation associated with the particular base used. The preferred catalyst is silver triflate.

After all reactants and reagents have been added, the reaction mixture is warmed to –0° C., stirred for 0.5–24 hours at 0° C. and then warmed slowly to room temperature. The reaction mixture is stirred for an additional 0.5–24 hours at room temperature. Generally, the reaction mixture is stirred at 0° C. for 5 hours and allowed to warm to room temperature over 3 hours followed by stirring at room temperature for 16 hours. The product is then isolated from the reaction mixture using techniques familiar to one of ordinary skill in the art. Thus, simple filtration through a filter aid such as Celite followed by evaporation affords a residue which is purified by column chromatography. One of ordinary skill in the art will recognize that column chromatography entails the use of a solid phase component such as silica gel and a liquid phase component comprised of an advantageous mixture of solvents for the separation and purification of compounds from a mixture. Removal of solvents after chromatography affords the glycosylmacrolide.

Generally, the coupling reaction only takes place at one of the three alcohol sites of the macrolide, this site being the C-4" alcoholic functionality (see Formula IV). This selectivity is possibly due to the greater availability of the hydroxyl group of this position in the macrolide's preferred conformation. On occasion, however, with particularly reactive sugar halides, small amounts of diglycosylated material (wherein $R^2=OR^0$) are formed. This material is detected during the monitoring of the progress of the reaction, which is generally accomplished via thin layer chromatography, according to standard practice. The diglycosylated material is isolated and purified as for the monoglycosylated material with the notable exception that the diglycosylated material is the first material isolated from the chromatography, with the monoglycosylated material being isolated in later fractions. The use of added equivalents of sugar chloride or the altering of other parameters such as solvent, base or catalyst can affect the yield of diglycosylated material.

To prepare the compound of formula (I) wherein $R^1$ is H and $R^0$ is a sugar substituent of the formula (II) or (III), a macrolide of formula (IV) or (V) is first protected with a hydroxyl protecting group at the c-4" position. Hydroxyl protecting groups suitable for such purposes include but are not limited to such groups as silyl ethers, carboxylic esters and carbonic esters of the alcohol. The protecting groups are appended to the alcohol utilizing the well known methods of organic chemistry. Bulky silyl ethers are preferred for their selectivity, ease of attachment and ease of removal. Conveniently, a macrolide of formula (IV) or (V) is dissolved in a reaction inert solvent at a temperature of about 0° C. to about 30° C. Reaction inert solvents for this type of reaction include dipolar aprotic solvents such as dimethylformamide, acetonitrile and N-methyl pyrrolidone; chlorinated solvents such as chloroform, dichloromethane and 1,2-dichloroethane; and ether solvents such as diethyl ether, dioxane and tetrahydrofuran. The solvent of choice is often dimethylformamide. A silylating agent, usually a silyltrifluoromethanesulfonate such as t-butyldimethylsilyltrifluoromethanesulfonate or a silyl chloride such as dimethyl-t-butylsilyl chloride, trimethylchlorosilane or triphenylchlorosilane, is added along with an organic amine such as triethylamine, trimethylamine or imidazole. Ordinarily imidazole is the preferred base. The reaction mixture is stirred for about one hour to about 24 hours, typically at room temperature, after which time the product is isolated from the reaction broth in a manner well known to one of ordinary skill in the art.

The macrolide, now protected at the C-4" position, can be coupled with a sugar halide of formula (VI) or (VII) as described hereinabove. The product of such a coupling reaction is a derivative of a compound of formula (I) with a sugar derivative attached by way of oxygen to the C-14 position and with a protected C-4" position. The C-4" position can be deprotected to afford the free hydroxy compound by employing standard methods of organic chemistry well known to one of ordinary skill in the art. Typically, to remove a preferred silyl ether protecting group, the C-4"-silyl protected compound of formula (I) is dissolved in a reaction inert solvent such as acetonitrile or an ether solvent such as tetrahydrofuran or diethyl ether at a temperature of about 0° C. to 30° C. and is treated with a fluoride source such as hydrogen fluoride or tetra-N-butylammonium fluoride. The reaction is stirred for about one hour to about 24 hours and the product is then isolated by employing standard methods of organic chemistry well known to one of ordinary skill in the art.

To prepare the compounds of the invention of formula (I) wherein A and B are taken separately and are each H (hereinafter referred to as the C-2 desoxo macrolide), a compound of formula (I) wherein A and B are taken together and are $=O$ is reduced using standard conditions for the reduction of a-ketoamides. This reduction procedure selectively reduces the carbonyl adjacent to the amide without affecting other carbonyls in the molecule. Generally the C-2 oxo macrolide of formula (I) is dissolved in a reaction inert solvent or mixture of solvents and hydrogen sulfide gas is bubbled through the mixture for 6–24 hours at room temperature. For convenience, the gas is generally bubbled through the reaction mixture overnight. Suitable reaction inert solvents for this reaction include, but are not limited to, organic bases such as diethylamine, triethylamine, dimethylamine, trimethylamine, piperidine, morpholine and aniline; dipolar aprotic solvents such as N,N-dimethylformamide, dimethylsulfoxide and N-methylpyrrolidone; and alcoholic solvents such as methanol, ethanol and propanol. A combination of two or more of these solvents is sometimes used to achieve optimum yield or to affect the course of reduction. For example, the macrolide wherein A is H and B is OH is prepared by using methanol as solvent. A particularly preferred solvent system for providing the C-2 desoxo macrolide is pyridine and N,N-dimethylformamide in equal amounts. When the reaction is completed, the product is isolated using the standard techniques of organic chemistry as would be understood by one of ordinary skill in the art.

Alternatively, the macrolide of formula (IV) or (V) can be reduced prior to glycosylation, using the foregoing procedure. Following reduction, the macrolide can be glycosylated as recited hereinabove.

To prepare compounds of the invention of formula (I) wherein the dotted line represents a bond and $R^2$ is hydrogen, the compound of formula (I) wherein $R^2$ is —OH and the dotted line represents no bond (hereinafter referred to as the β-hydroxy ketone) is dehydrated as disclosed in European Patent Application No. 323042. Generally the β-hydroxy ketone is dissolved in a reaction inert solvent containing a catalytic amount of an organic acid. Suitable reaction inert solvents are aromatic solvents such as benzene, toluene, xylene and the like, with toluene being preferred. The organic acid is generally selected from such acids as toluenesulfonic acid, camphorsulfonic acid and the like with toluenesulfonic acid being preferred. The reaction mixture is heated at about 50° C. to about 120° C. for about five minutes to about one hour. Generally steam bath temperatures (about 100° C.) are preferred and five minutes is generally sufficient for complete reaction. The reaction product is isolated according to methods well understood by one of ordinary skill in the art. The reaction is generally carried out on compounds which have already been glycosylated.

To prepare compounds of the invention of formula (I) wherein $R^5$, $R^6$ and $R^7$ are hydroxy and $R^4$ is hydroxymethyl, a compound of formula (I) wherein $R^5$, $R^6$ and $R^7$ are acetoxy and $R^4$ is acetoxymethyl is deacetylated using standard conditions known to one of ordinary skill in the art as recited hereinbelow. This selective deacetylation does not affect any amides which are present and is readily accomplished by the addition of an alkoxide base to a solution of the material to be deacetylated in an alcoholic solvent at 0° C. Generally a catalytic amount, such as 0.01 equivalents, of base is used. Usually the alkoxide base of the particular alcoholic solvent in use is preferred. Most preferred, for its ease of use and reactivity, is the system wherein methanol is the solvent and sodium methoxide is the base. Isolation of the product is achieved via standard methods well known to those of ordinary skill in the art.

The sugar halide derivatives of formulae (VI) and (VII) are conveniently prepared, when not readily available, from the readily available sugars of formulae (VIII) and (IX) wherein $R^{10}$ is H, ($C_1$–$C_4$)alkyl or ($C_2$–$C_4$)alkanoyl by employing standard methods of halogenation well known to one of ordinary skill in the art.

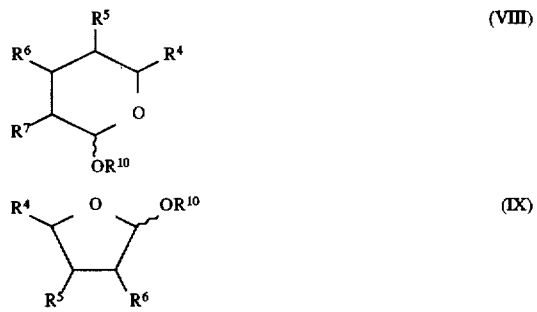

Bromination is the method of choice; chlorination may also be employed in certain cases. Bromination is effected by dissolving a 1-hydroxy, alkoxy or alkanoyloxy sugar derivative of formula (VIII) or (IX) in an organic acid solvent such as acetic acid. When the sugar is a 1-hydroxy or 1-alkoxy sugar, one to ten equivalents of acetic anhydride are generally added. The preferred substrates are 1-acetoxy sugar derivatives. The reaction mixture is cooled so that the temperature falls within the range of about −20° C. to about 0° C. The generally preferred temperature is about 0° C. The cooled reaction mixture is treated with a solution of hydrobromic acid in the acidic solvent. Generally a large excess, such as 10–40 molar equivalents, of hydrobromic acid is employed. The reaction mixture is warmed to room temperature and stirred until the reaction is complete. Generally, for convenience, the reaction mixture is left stirring overnight. The isolation of the brominated product is achieved in a straightforward manner well known to one of ordinary skill in the art. Often this merely involves removing the solvent in vacuo. Occasionally, to more fully effect solvent removal, a cosolvent, such as toluene, which azeotropes the reaction solvent is utilized. Further purification is sometimes achieved by the use of column chromatography.

To prepare compounds of formulae (VIII) and (IX) wherein $R^4$ is —$CH_2OCOR^8$; $R^5$, $R^6$ and $R^7$ are —$OCOR^8$; and $R^{10}$ is —$COR^8$, a compound of formulae (VIII) or (IX) wherein $R^4$ is —$CH_2OH$; $R^5$, $R^6$ and $R^7$ are —OH; and $R^{10}$ is H is used as a substrate in a standard acylation reaction. Typically said substrate is reacted with a suitable acylating agent such as, but not limited to, acetic anhydride, in a suitable solvent such as acetic acid at about 0° C. to about 25° C. The product is isolated utilizing the standard techniques of organic chemistry well known to one of ordinary skill in the art.

The sugar derivatives of formulae (VIII) and (IX) are generally readily available, being for the most part naturally occurring sugars.

The sugar derivatives of formula (VIII) and (IX) wherein R' is —COOH are readily available, being naturally occurring uronic acid derivatives of the corresponding sugars. The sugar derivatives of formlula (VIII) and (IX) wherein $R^4$ is —$CONH_2$, —$CONHR^8$, —$CONR_2^8$ or —$CO_2R^8$, when not readily available, are readily prepared utilizing well known methods of esterification or amidation known to one of ordinary skill in the art.

To prepare the compound of formula (I) wherein $R^4$ is —COOH, a sugar halide of formula (VI) or (VII) is coupled with a macrolide of formula (IV) or (V) as described hereinabove. After coupling, the —$R^8$ group is removed utilizing the standard de-esterification methods of organic chemistry known to one of ordinary skill in the art, providing a compound of formula (I) wherein $R^4$ is —COOH.

When the compounds of formula (I) of the present invention are acidic, as when $R^4$ is —$CO_2H$, the invention also embraces pharmaceutically acceptable salts of said compounds of formula (I).

Typical pharmaceutically acceptable cationic salts for such use include alkali metal salts (e.g., sodium and potassium), alkaline earth metal salts (e.g., magnesium and calcium), aluminum salts, ammonium salts and salts with organic amines such as benzathine (N,N'-dibenzylethylenediamine), choline, diethanolamine, ethylenediamine, meglumine(N-methylglucamine), benethamine(N-benzylphenethylamine),diethylamine, piperazine, tromethamine (2-amino-2-hydroxymethyl-1,3-propanediol) and procaine. An especially preferred such salt is the sodium salt.

The pharmaceutically acceptable cationic salts of the present invention are readily prepared by reacting the acid forms with an appropriate base, usually one equivalent, in a co-solvent. Typical bases are sodium hydroxide, sodium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

With respect to the macrolides of formula (I) of this invention, it is to be understood that there are conformer(s) or stereoisomeric forms such as optical and geometrical isomers due to asymmetric carbon atom(s) and double bond(s), and such isomers are also included within the scope of this invention.

The compounds of formula (I) thus prepared are useful in the treatment of resistance to transplantation and autoimmune diseases such as rheumatoid arthritis or psoriasis. In the treatment of resistance to transplantation, a compound of formula (I) may be used either prophylactically or in response to an adverse reaction by the human subject to a transplanted organ or tissue. When used prophylactically, a compound of formula (I) is administered to the patient or to the tissue or organ to be transplanted in advance of the transplantation operation. Prophylactic treatment may also include administration of the medication after the transplantation operation but before any signs of adverse reaction to transplantation are observed. When administered in response to an adverse reaction, a compound of formula (I)

is administered directly to the patient in order to treat said resistance to transplantation after outward signs of the resistance have been manifested.

For use in the treatment of resistance to transplantation and autoimmune diseases such as rheumatoid arthritis or psoriasis in a mammal, including man, a compound of formula (I) is formulated into a suitable pharmaceutical composition containing a disease treating effective amount. Depending upon the potency of the particular compound of formula (I) being administered, about 0.05 mg/kg of body weight per day to about 30 mg/kg of body weight per day, in single or multiple daily doses, is administered to the mammal being treated. A more preferred range is 0.1 mg/kg of body weight per day to about 20 mg/kg of body weight per day, although in particular cases, at the discretion of the attending physician, doses outside the broader range may be required. The preferred route of administration is generally oral, but parenteral administration (e.g., intravenous, intramuscular, subcutaneous or intramedullary) will be preferred in special cases such as where oral administration is inappropriate to the instant target or where the patient is unable for various reasons to ingest the drug. Topical administration may also be indicated, as where the patient is suffering from a skin disease such as psoriasis or whenever the medication is best applied to the surface of a tissue or organ as determined by the attending physician.

The compounds of formula (I) thus prepared are also useful in the treatment of infections caused by fungi. For use in the treatment of said fungal infections in a mammal, including man, a compound of formula (I) is formulated into a pharmaceutical composition containing a disease treating effective amount. Depending upon the potency of the particular compound of formula I being administered, about 0.05 mg/kg of body weight per day to about 30 mg/kg of body weight per day, in single or multiple daily doses, is the amount administered to the mammal being treated. A more preferred range is 0.1 mg/kg of body weight per day to about 20 mg/kg of body weight per day, although in particular cases, at the discretion of the attending physician, doses outside the broader range may be required. The preferred route of administration is generally oral, but parenteral administration (e.g., intravenous, intramuscular, subcutaneous or intramedullary) will be preferred in special cases such as where oral administration is inappropriate to the instant target or where the patient is unable for various reasons to ingest the drug. Topical administration may also be indicated whenever the medication is best applied to the surface of a tissue or organ as determined by the attending physician.

The compounds of the present invention are generally administered in the form of a pharmaceutical composition comprising at least one of the compounds of formula (I) together with a pharmaceutically acceptable vehicle or diluent. Such compositions are generally formulated in a conventional manner utilizing solid or liquid vehicles or diluents as appropriate to the mode of administration: for oral administration, in the form of tablets, hard or soft gelatin capsules, suspensions, granules, powders and the like; for parenteral administration, in the form of injectable solutions or suspensions and the like; and for topical administration, in the form of solutions, lotions, ointments, salves and the like.

The utility of the compounds of the present invention as medical agents in the treatment of resistance to transplantation and autoimmune diseases such as rheumatoid arthritis or psoriasis is demonstrated by the activity of said compounds in the biological screen described hereinbelow. Said biological screen also provides a means whereby the activities of the compounds of formula (I) can be compared with the activities of other known compounds. The results of these comparisons are useful for determining dosage levels in mammals, including man, for the treatment of resistance to transplantation and autoimmune diseases such as rheumatoid arthritis and psoriasis.

The human mixed lymphocyte reaction (MLR) is used to generate an immune response in vitro which is measured via $^3$H-thymidine uptake. This screen uses peripheral blood mononuclear cells in a modified two-way MLR. To ensure disparity of HLA type D antigens and therefore maximize stimulation, a pool of frozen donor cells is used as the stimulator population; freshly isolated cells are used as the responder population.

Freshly drawn mononuclear cells are suspended in RPMI-1640 enriched with: 0.5% MEM non-essential amino acids (100×) solution, 1% L-glutamine (200 mM), 1% MEM vitamins (100×), 1% penicillin streptomycin solution (10,000 units/mL) and 15% heat-inactivated human AB serum (NABI). The cells are counted and the concentration is adjusted to 5×10$^5$ cells/mL. The solution is then transferred to round bottom 96 well plates in 100 µL/well quantities. These plates now contain the responder cells.

The stimulator cells are prepared by pooling the mononuclear cells collected from several different individuals. The cells are suspended in 90% human AB serum and 10% DMSO such that the cell count is 2×10$^7$ cells/mL. The cells are stored in liquid nitrogen. For an MLR, the viable cells are diluted to 5×10$^5$ cells/mL, and 100 µL/well is added to the plates containing the responder cells. To each well, containing a mixture of responder cells and stimulator cells, is added 50 µL of compound solution. Triplicate wells are run for each dose. The plates are incubated at 37° C. under an atmosphere of 5% $CO_2$ and are humidified for five days. To each well is added 1 µCi of $^3$H-thymidine and incubation is continued for another eighteen hours. The cells are harvested using the LKB Beta Plate system.

The percent inhibition of stimulated control is obtained using the following equation:

$$\% \text{ Inhibition} = \left[ 100 - \left( \frac{\text{avg. } cpm \text{ of drug}}{\text{avg. } cpm \text{ of stimulated control}} \right) \right] \times 100$$

The abbreviation cpm is defined as counts per minute. RPMI-1640 is a tissue culture medium which is available from Sigma.

Activity in the MLR screen recited above is indicative of usefulness of the active compound in the treatment of resistance to transplantation and autoimmune diseases such as rheumatoid arthritis and psoriasis.

Antimicrobial activities of the macrolides of the present invention against various fungi are determined by a serial agar dilution method in a Sabouraud agar. Minimum inhibitory concentrations (MIC) are obtained after incubation for 24 hours at 30° C.

The present invention is illustrated by the following examples. However, it should be understood that the invention is not limited to the specific details of these examples. All reactions are conducted under an inert atmosphere, such as nitrogen, unless otherwise specified. The abbreviations THF, DMSO, DAST, DMAP and Ac, where used, refer to tetrahydrofuran, dimethyl sulfoxide, dimethylamino sulfurtrifluoride, 4-dimethylaminopyridine and acetyl, respectively. The sugar halides were purchased from a reliable vendor such as Sigma or Aldrich, as were the sugars, unless specifically mentioned. Anhydrous solvents were used, anhydrous being defined as substantially free from water.

The expression "reaction inert solvent," where used hereinabove, refers to any solvent which does not interact with starting materials, reagents, intermediates or products in a manner which adversely affects the yield of the desired product.

Terms or acronyms which appear in Preparations 1 and 2 are described in further detail hereinbelow.

PYEA agar is prepared by dissolving Difco maltose (10 g), Difco yeast extract (4 g), dextrose (4 g), Difco agar (15 g) and fresh coconut milk (50 mL) in enough deionized water to yield a one liter solution; and the solution is adjusted to pH 7.3 with 1N NaOH.

ATCC 172 medium is prepared by dissolving glucose (10 g), soluble starch (20 g), yeast extract (5 g), NZ-amine A (Difco, 5 g) and calcium carbonate (1 g) in enough deionized water to yield a one liter solution; and the solution is adjusted to pH 7.0 with 1N KOH.

JDYTT medium is prepared by dissolving cerelose (10 g), corn starch (5 g), corn steep liquor (5 g), NZ-amine YTT (5 g), cobalt chloride (0.002 g) and calcium carbonate (3 g) in enough deionized water to yield a one liter solution; and the solution is adjusted to pH 7.2 with 1N NaOH.

NZ-amine A and NA-amine YTT are available from Difco, as are most of the ingredients of the above media.

In the MLR protocol provided hereinabove, RPMI-1640 is a standard medium for MLR studies; MEM is defined as "minimum essential media"; and NABI is a supplier.

EXAMPLE 1

17-Ethyl-1,14-dihydroxy-12-[2'-(4"-(2'",3'",4'"-tri-O-acetyl-α-D-fucopyranosyloxy)-3"-methoxycyclohexyl)-1'-methylvinyl]-23,25-dimethoxy-13,19,21,27-tetramethyl-11, 28-dioxa-4-azatricyclo[22.3.1.0$^{4,9}$]-octacos-18-ene-2,3,10, 16-tetraone To a stirred slurry of the title compound of Preparation 1 (6.41 g, 0.0081 mmol), α-L-acetochlorofucose (Sigma, 5.0 g, 0.016 mmol) and 4 Å Molecular sieves (crushed, 5.0 g) in methylene chloride (anhydrous, 150 mL) at −78° C. was added silver carbonate (13.36 g, 0.0324 mmol) followed by silver triflate (0.83 g, 0.0032 mmol). The reaction mixture was allowed to warm to room temperature over eight hours and was then stirred for an additional five hours. The resultant tan slurry was filtered through Celite and the filtrate was evaporated in vacuo. The residue was purified on silica gel, eluting with hexane/ethyl acetate (2/1) to afford the product as a mixture of anomers (9.0 g, 52%).

EXAMPLES 2–11

By the method of Example 1, but substituting one molar equivalent of the appropriate sugar chloride for each molar equivalent of α-L-acetochlorofucose, the following compounds were prepared.

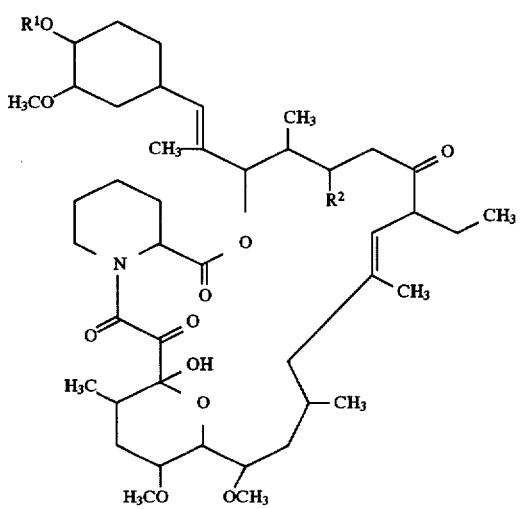

| | R$^1$ | R$^2$ | Yield |
|---|---|---|---|
| 2. | BnO-sugar(OBn, BnO, OBn) | —OH | Mass spectrum (FAB): m/z = 1216.7 (molecular ion + Na$^+$) $^{13}$C-NMR: δ 169.0, 164.7, 138.7, 138.4, 138.3, 137.8, 132.5, 123.0 |
| 3. | sugar(OAc, AcO, AcO, CH$_3$) | —OH | Mass spectrum (FAB): m/z = 1086.7 (molecular ion + Na$^+$) $^{13}$C-NMR: δ 213.4, 196.2, 170.8, 170.2, 170.0 |
| 4. | sugar(OAc, AcO, AcO, OAc) | —OH | Mass spectrum (FAB): m/z = 1144.7 (molecular ion + Na$^+$) $^{13}$C-NMR: δ 213.2, 196.3, 171.4 170.5, 170.1, 170.0, 165.1 |
| 5. | sugar(AcO, CH$_3$, AcO, OAc) | —OH | Mass spectrum (FAB): m/z = 1086.7 (molecular ion + Na$^+$) $^{13}$C-NMR: δ 213.5, 196.2, 170.7, 170.2, 169.4, 168.9 |
| 6. | sugar(CO$_2$CH$_3$, AcO, AcO, OAc) | —OH | Mass spectrum (FAB): m/z = 1130.7 (molecular ion + Na$^+$) $^{13}$C-NMR: δ 213.4, 196.2, 169.4, 169.2, 167.3 |
| 7. | sugar(OAc, AcO, AcO, OAc) | —OH | Mass spectrum (FAB): m/z = 1144.7 (molecular ion + Na$^+$) $^{13}$C-NMR: δ 213.2, 196.1, 171.5, 171.2, 170.8, 170.0, 163.1 |
| 8. | sugar(OAc, AcO, AcO, AcO) | —OH | Mass spectrum (FAB): m/z = 1144.7 (molecular ion + Na$^+$) $^{13}$C-NMR: δ 213.4, 196.2, 170.8, 170.2, 169.9, 169.2 |
| 9. | sugar(AcO, AcO, OAc) | —OH | Mass spectrum (FAB): m/z = 1072.7 (molecular ion + Na$^+$) |
| 10. | sugar(AcO, AcO, OAc) | —OH | Mass spectrum (FAB): m/z = 1072.7 (molecular ion + Na$^+$) |

EXAMPLE 12

To a stirred solution of the title compound of Example 1 (1.0 g, mmol) in methanol (100 mL) was added sodium methoxide (20 mg, mmol). The reaction mixture was stirred at 0° C. for eight hours and then treated with one drop of acetic acid. The solvent was removed in vacuo and the residue was purified on silica gel, eluting with THF to afford 610 mg of a foam (72%). Mass spectrum (FAB): m/z=960.6 (molecular ion+Na$^+$).

EXAMPLES 13–21

By the method of Example 12, but substituting one molar equivalent of the appropriate title compound of Examples 2-11 for each molar equivalent of the title compound of Example 1, the following compounds were prepared.

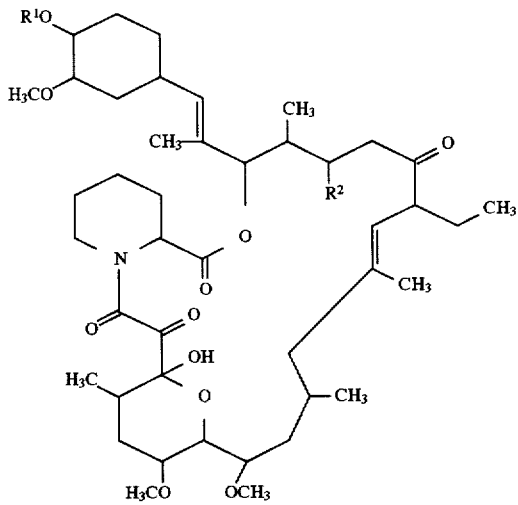

| | R¹ | R² | Yield | |
|---|---|---|---|---|
| 13. | OH, O, HO, HO, OH, OH (sugar) | —OH | Mass spectrum (FAB): m/z = 976.6 (molecular ion + Na⁺) ¹³C-NMR: δ 212.0, 196.8, 169.3, 166.1, 139.1, 138.5, 132.4, 131.8, 123.5 | |
| 14. | OH, OH, O, HO, HO (sugar) | —OH | Mass spectrum (FAB): m/z = 976.6 (molecular ion + Na⁺) ¹³C-NMR: δ 213.4, 198.5, 170.6, 167.5, 140.5, 139.8, 133.4, 125.0 | |
| 15. | OH, CH₃, O, HO, OH (sugar) | —OH | Mass spectrum (FAB): m/z = 960.6 (molecular ion + Na⁺) | |
| 16. | OH, OH, O, HO, OH (sugar) | —OH | Mass spectrum (FAB): m/z = 976.6 (molecular ion + Na⁺) ¹³C-NMR: δ 212.1, 197.0, 169.2, 166.0, 139.1, 138.5, 132.2, 131.8, 131.0, 123.5 | |
| 17. | OH, O, HO, CH₃, OH (sugar) | —OH | Mass spectrum (FAB): m/z = 960.6 (molecular ion + Na⁺) ¹³C-NMR: δ 212.0, 197.0, 169.3, 166.7, 166.0, 138.4, 132.0, 131.6, 123.5 | |
| 18. | CO₂CH₃, O, HO, HO, OH (sugar) | —OH | Mass spectrum (FAB): m/z = 1004.6 (molecular ion + Na⁺) ¹³C-NMR: δ 213.4, 197.1, 169.8, 168.4, 166.1 | |
| 19. | OH, O, HO, OH (sugar) | —OH | Mass spectrum (FAB): m/z = 946.5 (molecular ion + Na⁺) ¹³C-NMR: δ 213.4, 196.2, 169.0, 164.7, 138.7, 137.8, 132.4 | |

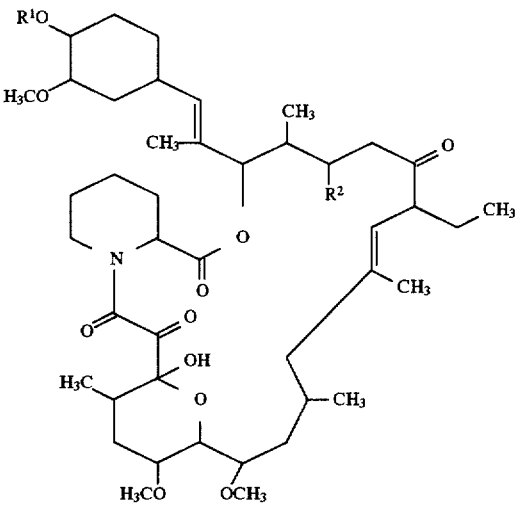

| | R[1] | R[2] | Yield |
|---|---|---|---|
| 20. | with OAc | —OH | Mass spectrum (FAB): m/z = 946.5 (molecular ion + Na+) $^{13}$C-NMR: δ 213.2, 196.0, 168.8, 165.0, 138.5, 137.8, 133.1 |

EXAMPLE 21

17-Ethyl-1,14-dihydroxy-12-[2'-(4"-(2'",3'",4'"-tri-O-acetyl-α-D-rhamnopyranosyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-3,10,16-trione The title compound of Example 3 (1.0 g) was dissolved in DMF (15 mL) and pyridine (15 mL) and hydrogen sulfide gas was bubbled through the reaction mixture for 16 hours at room temperature. Excess hydrogen sulfide was prevented from escaping into the atmosphere by means of a Chlorox trap. After 16 hours, the reaction mixture was diluted with toluene (50 mL) and washed with brine (50 mL). The solvent was dried with MgSO$_4$ and the solvent was removed in vacuo. The residue was passed through a pad of silica gel and eluted with ethyl acetate/hexane (2/1) to afford the title compound. Mass spectrum (FAB): m/z=1072.7 (molecular ion+Na+). [13]C—NMR: δ215.3, 174.0, 170.3, 170.1, 169.4, 141.1 and 132.6.

PREPARATION 1

17-Ethyl-1,14-dihydroxy-12-[2'-(4"-hydroxy-3"-methoxy-cyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone

*Streptomyces hygroscopicus* subsp. *ascomyceticus* culture ATCC 14891 was carried on PYEA agar slants (10 g/L of Difco maltose, 4 g/L of Difco yeast extract, 4 g/L of dextrose, 15 g/L of Difco agar and 50 mL of fresh coconut milk which was diluted up to one liter with deionized water, then adjusted to pH 7.3 with 1N NaOH). The preparation was incubated for 10 to 12 days at 28° C., and the spores were then transferred to sterile 1×6 shake tubes containing 10 mL of ATCC 172 medium (10 g/L of glucose, 20 g/L of soluble starch, 5 g/L of yeast extract, 5 g/L of NZ-amine A and 1 g/L of calcium carbonate. The pH was adjusted to 7.0 with 1N KOH). The tubes were incubated at 28° C. and shaken on a rotary shaker at about 150 to 200 cycles/minute. After 4 to 5 days the broth was diluted to 40% with glycerol and ATCC 172 medium and then transferred aseptically to cryotubes. Each tube was charged with ½ mL of broth. The tubes were frozen at −80° C. during storage.

The tubes from the ultra cold stock were used as seed innoculum for the preparation of innoculum flasks, one tube per 50 mL of sterile JDYTT medium in 300 mL shake flasks. The composition of the JDYTT medium was 10 g/L of cerelose, 5 g/L of NZ-amine YTT, 0.002 g/L of cobalt chloride and 3 g/L of calcium carbonate. The pH of the JDYTT medium was adjusted to pH 7.2 with 1N NaOH. The shake flasks were shaken and incubated on a rotary shaker at about 150–200 cycles/minute and 28° C.

Two mL of an about 3 to 5 day-old shake flask innoculum was used to innoculate the second stage flask innoculum containing 80 mL of JDYTT medium in a 3 L jar fermenter. The fermenter medium was 45 g/L of corn starch, 10 g/L of corn steep liquor, 10 g/L of amber or Baker dried yeast, 3 g/L of calcium carbonate and 0.005 g/L of cobalt chloride. The pH was adjusted to about 6.4 to 6.8 with 1N NaOH. One mL of antifoam P-2000 was added to the jar fermenters together with 100 mL of soya bean oil. The pH was adjusted to about 6.4 to 6.8 with 1N NaOH and the material was agitated at 1700 rpm. The temperature was maintained at 28° C. and sterile air was sparged through the medium at the rate of one volume per volume per minute.

After innoculation, sterile soya bean oil was used to control foaming. In longer fermentations, and, depending on media used, the sugar content can be monitored and sugar feeds used at 40, 60 and 90 hours to maintain the reducing sugar level at or above 0.05%. The fermentation was run for 46 hours.

Using standard methods of thin-layer chromatography and HPLC, the fermentation broth was monitored and relative potency was calculated.

The product was found primarily in the mycelium, but workup of the whole broth is preferred. Thus, after the fermentation has run its course, the whole broth was extracted twice with one-third to one-half of its volume of methylisobutylketone (MIBK). The layers were separated by means of a DeLaval separator or a Podbielnack extractor. The solvent layer was clarified and concentrated first in a vacuum pan and then in a rotary evaporator. The concentrate was subjected to four tube counter current distribution in 20 liter carbuoys using 10 liter top layer and 1 liter bottom layer per carbuoy of a heptane/acetonitrile 10/1 system. The active bottom layers were collected, combined and concentrated. The material was further purified via filtration through Florisil (washing with hexane, hexane/methylene chloride and methylene chloride, successively, with a gradual increase in methylene chloride). Most of the activity was found in the methylene chloride fractions. These were combined and concentrated. A second filtration step was performed, this time through silica gel (washing with heptane, methylene chloride, methylene chloride/ethyl acetate and ethyl acetate). The activity was mostly found in the fractions containing a methylene chloride/ethyl acetate mixture and the fractions containing only ethyl acetate. These were combined and concentrated, redissolved in methylene chloride and treated with DARCO G60. The sample was then divided into 12 to 15 g portions and each sample was further chromatographed on a Prep 500 liquid chromatograph using silica gel columns and eluting using a linear gradient beginning with 100% methylene chloride and ending with 100% ethyl acetate. The active cuts were combined, concentrated and chromatographed on a Prep 500, using reversed phase ($^{18}$C) silica gel and eluting with a linear gradient beginning with acetone and ending with 100% water. Clean product was obtained as the last component isolated off the column.

The active fractions in the foregoing fermentation procedure were determined using the following bioassay.

A 12.5 mm disc was applied directly to the agar surface. *Candida albicans* ATCC 14053, *Saccharomyces pastorianus* FD3737 and a sensitive strain of *Byssochlamys fulva* FM 10.300(S) and FM 10.464(R) were used. The Candida and Saccharomyces plates were incubated at 37° C. for 18 hours, then the plates were examined for activity. The Byssochlamys plates were incubated at 28° C. and read after 18 hours. Plates containing only FK506 and FK520 (CP-105051) were active against the Byssochlamys strain. Impure fractions (containing nigericin) were active against the other strains as well.

An HPLC method for determining the purity of the fractions was also used. The method entailed using a Dupont Zorbax CN column (4.6 mm×25 cm) and an isocratic system composed of 55/45 water/acetonitrile and a flow rate of one mL/min. Detection was accomplished at 214 nm. The broth sample (20 mL) was mixed with MIBK (20 mL) and shaken for about 4 to 5 minutes. The layers were separated and the solvent was concentrated to near dryness. The residue was taken up in 1 mL of neat acetonitrile and a 5 µL sample was injected into the HPLC. The retention time for FK520 is approximately 12.7 minutes under these conditions.

PREPARATION 2

17-Allyl-1,14-dihydroxy-12-[2'-(4"-hydroxy-3"-methoxy-cyclohexyl)-1'-methylvinyl]-23,25-dimethoxy-13, 19,21,27-tetramethyl-11,28-dioxa-4-azatricyclo-[22.3.1.0$^{4,9}$]-octacos-18-ene-2,3,10,16-tetraone

*Streptomyces tsukubaensis* No. 9993 FERM BP-927 was carried on PYEA agar slants (10 g/L of Difco maltose, 4 g/L of Difco yeast extract, 4 g/L of dextrose, 15 g/L of Difco agar and 50 mL of fresh coconut milk which was diluted up to one liter with deionized water, then adjusted to pH 7.3 with 1N NaOH). The preparation was incubated for 10 to 12 days at 28° C., and the spores were then transferred to sterile 1×6 shake tubes containing 10 mL of ATCC 172 medium (10 g/L of glucose, 20 g/L of soluble starch, 5 g/L of yeast extract, 5 g/L of NZ-amine A and 1 g/L of calcium carbonate. The pH was adjusted to 7.0 with 1N KOH). The tubes were incubated at 28° C. and shaken on a rotary shaker at about 150 to 200 cycles/minute. After 4 to 5 days the broth was diluted to 40% with glycerol and ATCC 172 medium and then transferred aseptically to cryotubes. Each tube was charged with ½ mL of broth. The tubes were frozen at −80° C. during storage.

The tubes from the ultra cold stock were used as seed innoculum for the preparation of innoculum flasks, one tube per 50 mL of sterile JDYTT medium in 300 mL shake flasks. The composition of the JDYTT medium was 10 g/L of cerelose, 5 g/L of NZ-amine YTT, 0.002 g/L of cobalt chloride and 3 g/L of calcium carbonate. The pH of the JDYTT medium was adjusted to pH 7.2 with 1N NaOH. The shake flasks were shaken and incubated on a rotary shaker at about 150–200 cycles/minute and 28° C.

Two mL of an about 3 to 5 day-old shake flask innoculum was used to innoculate the second stage flask innoculum containing 80 mL of JDYTT medium in a 3 L jar fermenter. The fermenter medium was 45 g/L of corn starch, 10 g/L of corn steep liquor, 10 g/L of amber or Baker dried yeast, 3 g/L of calcium carbonate and 0.005 g/L of cobalt chloride. The pH was adjusted to about 6.4 to 6.8 with 1N NaOH. One mL of antifoam P-2000 was added to the jar fermenters together with 100 mL of soya bean oil. The pH was adjusted to about 6.4 to 6.8 with 1N NaOH and the material was agitated at 1700 rpm. The temperature was maintained at 28° C. and sterile air was sparged through the medium at the rate of one volume per volume per minute.

After innoculation, sterile soya bean oil was used to control foaming. In longer fermentations, and, depending on media used, the sugar content can be monitored and sugar feeds used at 40, 60 and 90 hours to maintain the reducing sugar level at or above 0.05%. The fermentation was run for 46 hours.

Using standard methods of thin-layer chromatography and HPLC, the fermentation broth was monitored and relative potency was calculated.

The fermenters were stopped and extracted twice with ½ its volume of methylisobutylketone (MIBK). The solvent layer was separated by aspiration and concentration in vacuo to a viscous oil. The oil was triturated with hexane, diethyl ether and methylene chloride and the active cuts (the diethyl ether cuts) were chromatographed on florisil. The florisil was eluted with, successively, diethyl ether methylene chloride, ethyl acetate and acetone. The eluate was concentrated and treated with activated charcoal. The concentrate was filtered and dissolved in ethyl acetate. Hexane was added to crystallize the product.

The bioactivity of the broth and subsequent recovery streams was followed by using a strain of *Byssochlamys fulva*. The components in the broth and recovery streams were visualized by chromatography on Analtech silica gel GF (Trademark) plates using neat ethyl acetate as the eluant. The developed plates were sprayed with vanillin reagent (3 g of vanillin in 75 mL of ethanol and 25 mL of 85% phosphoric acid) and heated to 80° C. The product appeared as a violet spot.

PREPARATION 3

2,3,5-Tri-O-benzyl-β-arabinofuranosyl Bromide 2,3,5-Tri-O-benzyl-1-O-p-nitrobenzoyl-β-arabinofuranoside (Sigma, 5.69 g, 10 mmoles) was dissolved in methylene chloride (25 mL) at 0° C. and treated with 33% HBr in acetic acid (Fluka, 25 mL). The mixture was stirred at room temperature for two hours. The solvent was removed in vacuo and the residue was azeotroped from toluene to afford a brownish oil. Yield 98% used as is.

PREPARATIONS 4-6

By performing the procedures described by Kartha, K. P. R. and H. J. Jennings, Journal of Carbohydrate Chemistry, 9, 777-781 (1990), the following compounds were prepared.

4. 2,3,4-Tri-O-acetyl-β-arabinosyl bromide
5. 2,3 4-Tri-O-acetyl-α-arabinosyl bromide
6. 2,3,4-Tri-O-acetyl-β-rhamnosyl bromide

I claim:

1. A compound of the formula

[structure]

or a pharmaceutically acceptable salt thereof;
wherein n is 1 or 2;
the dotted line represents an optional double bond in the case where $R^2$ is H;
A and B are taken separately and are each independently H or OH, or A and B are taken together and form =O;
$R^2$ is H, ($C_2$-$C_5$)alkanoyloxy or —$OR^o$;
$R^3$ is ($C_1$ to $C_3$)alkyl or allyl;
$R^1$ and $R^o$ are each H,

[structures]

$R^4$ is, for each occurrence, independently —$CO_2R^8$, —$CO_2H$, —$CH_2OH$, H, —$CH_3$, —$CONH_2$, —$CONHR^8$, —$CONR_2^8$, —$CH_2OCOR^8$, —$CH_2OCO_2R^8$, —$CH_2OCONHR^8$, —$CH_2OCONR_2^8$ or —$CH_2OR^8$;

$R^5$, $R^6$ and $R^7$ are, for each occurrence, independently ($C_1$ to $C_4$) alkoxy, benzyloxy, —OH, —$OCOR^8$, —$OCO_2R^8$ or —$OSi(R^9)_3$;

$R^8$ is ($C_1$ to $C_6$)alkyl, ($C_3$ to $C_6$)cycloalkyl, allyl, pyridyl, thienyl, benzyl, benzyl substituted with one to five halogen atoms, —OH groups, or ($C_1$ to $C_4$)alkoxy groups, phenyl or phenyl substituted with one to five halogen atoms, —OH groups or ($C_1$ to $C_4$) alkoxy groups; and $R^9$ is, for each occurrence, independently ($C_1$ to $C_4$)alkyl, phenyl or benzyl; provided that when $R^1$ is H, then $R^2$ is —$OR^o$ and $R^o$ is

[structures]

2. A compound according to claim 1 wherein the dotted line represents no bond and $R^2$ is —OH.

3. A compound according to claim 2 wherein n is 2 and A and B are taken together and form =O.

4. A compound according to claim 3 wherein $R^3$ is methyl, ethyl or allyl.

5. A compound according to claim 4 wherein $R^3$ is ethyl.

6. A compound according to claim 5 wherein $R^1$ is

[structures]

7. A compound according to claim 6 wherein $R^4$ is —$CH_2OH$, —$CH_3$, —$CH_2OCOCH_3$, —$CH_2OCOCH_2C_6H_3$, or —$CO_2CH_3$; and $R^5$, $R^6$ and $R^7$ are each, independently, —OH, $OCOCH_3$ or —$OCOCH_2C_6H_5$.

8. A compound according to claim 7 wherein $R^1$ is

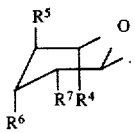

9. The compound according to claim 8 wherein $R^4$ is —$CH_3$, $R^5$ is —$OCOCH_3$, $R^6$ is —$OCOCH_3$ and $R^7$ is —$OCOCH_3$.

10. The compound according to claim 8 wherein $R^4$ is —$CH_3$, $R^5$ is —OH, $R^6$ is —OH and $R^7$ is —OH.

11. A compound according to claim 7 wherein $R^1$ is

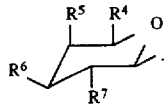

12. The compound according to claim 11 wherein $R^4$ is —$CH_2OCOCH_3$ and $R^5$, $R^6$ and $R^7$ are each —$OCOCH_3$.

13. The compound according to claim 11 wherein $R^4$ is —$CH_2OCOCH_3$ and $R^5$, $R^6$ and $R^7$ are each —OH.

14. A compound according to claim 1 wherein n is 2; A and B are taken separately and are each H; the dotted line represents no bond; $R^2$ is —OH and $R^3$ is ethyl.

15. The compound according to claim 14 wherein $R^1$ is

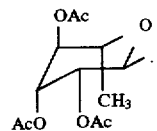

16. A compound according to claim 1 wherein n is 2; A and B are taken together and form =O; the dotted line represents no bond; $R^2$ is $OR^0$; $R^3$ is ethyl and $R^0$ and $R^1$ are each

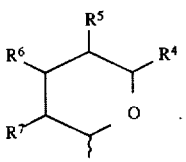

17. A method for treating resistance to transplantation in a mammal in need of such treatment comprising administering to said mammal a resistance to transplantation treating effective amount of a compound according to claim 1 or a pharmaceutically-acceptable salt thereof.

18. A method for treating autoimmune disease in a mammal in need of such treatment comprising administering to said mammal an autoimmune disease treating effective amount of a compound according to claim 1 or a pharmaceutically-acceptable salt thereof.

19. A method for treating fungal diseases in a mammal in need of such treatment comprising administering to said mammal a fungal disease treating effective amount of a compound according to claim 1 or a pharmaceutically-acceptable salt thereof.

20. A pharmaceutical composition comprising a resistance to transplantation treating effective amount of a compound of claim 1 and a pharmaceutically-acceptable carrier.

21. A pharmaceutical composition comprising an autoimmune disease treating effective amount of a compound of claim 1 and a pharmaceutically-acceptable carrier.

22. A pharmaceutical composition comprising a fungal disease treating effective amount of a compound of claim 1 and a pharmaceutically-acceptable carrier.

* * * * *